(12) United States Patent
Petit

(10) Patent No.: US 10,201,341 B2
(45) Date of Patent: Feb. 12, 2019

(54) SPINAL DEVICE COMPRISING MEANS OF REVERSIBLE FASTENING

(71) Applicant: SAFE ORTHOPAEDICS, Eragny sur Oise (FR)

(72) Inventor: Dominique Petit, Verton (FR)

(73) Assignee: SAFE ORTHOPAEDICS, Eragny Sur Oise (FR)

( * ) Notice: Subject to any disclaimer, the term of this patent is extended or adjusted under 35 U.S.C. 154(b) by 879 days.

(21) Appl. No.: 14/402,444

(22) PCT Filed: May 28, 2013

(86) PCT No.: PCT/FR2013/051191
§ 371 (c)(1),
(2) Date: Feb. 24, 2015

(87) PCT Pub. No.: WO2013/178940
PCT Pub. Date: Dec. 5, 2013

(65) Prior Publication Data
US 2015/0164495 A1    Jun. 18, 2015

(30) Foreign Application Priority Data
May 28, 2012   (FR) ...................................... 12 54895

(51) Int. Cl.
*A61B 1/32*     (2006.01)
*A61B 17/02*    (2006.01)
*A61B 17/70*    (2006.01)

(52) U.S. Cl.
CPC ........ *A61B 17/0206* (2013.01); *A61B 17/708* (2013.01); *A61B 17/7085* (2013.01); *A61B 17/7091* (2013.01); *A61B 2017/0256* (2013.01)

(58) Field of Classification Search
None
See application file for complete search history.

(56) References Cited

U.S. PATENT DOCUMENTS

| | | | |
|---|---|---|---|
| 3,509,873 A | 5/1970 | Karlin et al. | |
| 2006/0189997 A1* | 8/2006 | Guenther | ........... A61B 17/1728 606/88 |
| 2006/0264962 A1 | 11/2006 | Chin et al. | |
| 2008/0262318 A1 | 10/2008 | Gorek et al. | |
| 2010/0198268 A1 | 8/2010 | Zhang et al. | |

FOREIGN PATENT DOCUMENTS

| | | |
|---|---|---|
| EP | 0455282 A2 | 11/1991 |
| FR | 2874496 A1 | 3/2006 |
| FR | 2954689 A1 | 7/2011 |
| WO | 2011080426 A2 | 7/2011 |

* cited by examiner

*Primary Examiner* — Sameh Boles
(74) *Attorney, Agent, or Firm* — Bachman & LaPointe, P.C.

(57) ABSTRACT

A spinal device for carrying out a surgical procedure on vertebrae by a posterior or posterolateral approach, including at least one tube, at least one spinal screw capable of engaging with the proximal end of a tube, wherein the device also comprises a connection accessory, having means of reversible fastening to at least one of said tubes, said connection part being configured such as to keep at least one of said tubes in an open angular position.

4 Claims, 11 Drawing Sheets

SPINAL DEVICE COMPRISING MEANS OF REVERSIBLE FASTENING

BACKGROUND

The present invention relates to the field of surgical instruments for spinal stabilisation operations using bone-anchor elements such as screws by a posterior or posterolateral approach.

The invention relates specifically to an instrument kit according to the invention intended mainly, but not exclusively, for lumbar, thoracic or even posterior cervical spinal osteosynthesis surgery, by minimally invasive or open surgical approaches.

In the event of anatomical malfunctions of the spinal column, bone anchors such as pedicular or vertebral screws are placed in the vertebra, connected to one another by connection elements such as rods or plates.

PRIOR ART

Patent application PCT/FR10/000880, by the applicant, is known from the prior art. Said document discloses instrumentation for fixing at least two spinal vertebrae by bone-anchor implants such as pedicular screws including a bone-anchor element intended for being fixed to a vertebra, pre-mounted on a disposable mounting tube, and a sealed sterile packaging container.

Said prior art document also relates to a kit of instruments for installing or removing a spinal implant comprising at least two threaded bone-anchor elements, a connecting member such as a rod or a plate mechanically connecting the bone-anchor elements and locking elements for locking the connecting member in position relative to the anchor elements, in order to perform all the surgical deeds linked to the installation or removal of said implant, characterised in that all of said necessary instruments are disposable and packaged under sterile conditions in one or more sealed containers.

French patent FR2874496 is also known, describing a retractor for the tissues of a patient, of the type including two blades having a proximal end and a distal end, respectively, said blades being arranged such as to form a surgical channel open at the proximal and distal ends of said blades, characterised in that the retractor comprises at least one matching blade to form a retractor with at least three blades, said blades separating from one another by pivoting the distal ends thereof such as to form a tapering widened surgical channel.

European patent application EP0455282 is also known, describing an autostatic separator including a polygonal winder frame connected to a plurality of dilators.

When inserted deeply into the body of the patient, it keeps the edges of the incision open. The sides are hingedly connected to one another and to two opposing hinges.

Another example of a separator is described in U.S. Pat. No. 3,509,873.

DRAWBACKS OF THE PRIOR ART

Said prior art retractor solutions have two major drawbacks. First of all, these solutions lead to two separate devices:
one or more tubes making it possible to support the spinal screw and, during the intervention, to guide the linking rod which is inserted in the screw head, and then to insert and screw a plug locking the rod in the screw head;
a second device made up of a plurality of blades capable of holding the tissues in the area around the operating area.

In the prior art solutions, said known devices take up a considerable amount of space in the surgical area, which makes it necessary either to widen the incision, or to make do with a narrow field of vision and work. In both these cases, the surgeon is impeded in the execution of the operation and the surgical deed.

The second drawback is that the second device must be positioned prior to inserting the screws. Once it is placed in the operating area, the device limits the possible angulation of the tubes and thus complicates spinal screwing and the insertion of the proximal end of the tube on the spinal screw when the screw is not pre-mounted on the tube.

Finally, in all the prior art solutions, the retractor (second device) is a complex surgical instrument, requiring thorough, complicated sterilisation, given the complex shapes and the presence of multiple hinged sections, after each use. Said complex additional device furthermore creates an additional cost which is difficult to afford given the economic constraints of the healthcare industry.

SUMMARY

In order to solve the drawbacks of the prior art, the present invention proposes a solution that consists of completing the spinal tube(s) by a simple accessory at least making it possible to use the tube not only for the initial function thereof of installing the spinal screw, inserting the linking rod and tightening the plug, but also to grant the tube(s) an additional function of retracting the tissues.

For this purpose, the invention relates, in its broadest sense, to a spinal device for carrying out a surgical procedure on vertebrae by a posterior or posterolateral approach, characterised by including at least one tube, at least one spinal screw capable of engaging with the proximal end of a tube, characterised in that the device also comprises a connection accessory, having means of reversible fastening to at least one of said tubes, said connection part being configured such as to keep at least one of said tubes in an open angular position.

"Open angular position" is understood to be a position in which a generatrix of the tube is divergent, at the distal end, with the longitudinal axis of the spinal screw.

Advantageously, the device includes two tubes each formed by two half shells capable of engaging with the head of a spinal screw such as to allow proximal tilting of at least one of said half shells relative to the head of said spinal screw, said connection accessory being configured such as to keep two of said half shells in an open angular position.

According to a first alternative embodiment, said connection accessory is made up of a part which can adapt to said two half shells of a single tube, said part having a median portion extended at either side by an area for reversible fastening capable of engaging with a matching distal area of one of said half shells, in order to lock said half shells in the open position thereof.

Advantageously, said connection part has two opposite areas for reversible fastening to a frontal area of one of said half shells, said areas having an inner surface that matches the outer surface of the frontal area of the half shells.

According to a second alternative embodiment, which is not exclusive to the first alternative embodiment, said connection accessory is made up of a rigid retraction blade capable of engaging with two separate tubes and of keeping the tissues in the area around the surgical field separated by locking the relative position of two tubes.

According to a specific embodiment, the device includes two tubes each made up of two half shells, two spinal screws and two connection accessories.

The invention also relates to an accessory for connecting two half shells, characterised by being made up of a rigid part having means of reversible fastening to said half shells, said connection part being configured to keep said half shells in an open position.

The invention also relates to a retraction blade for carrying out a surgical procedure on vertebrae by a posterior or posterolateral approach, characterised by being made up of a rigid blade capable of engaging with two separate tubes and of keeping the tissues in the area around the surgical field separated.

Such a connection accessory and such a retraction blade are the components of a device according to the invention. Said components can be used together or separately to implement the invention, consisting of providing the spinal tubes with an additional function of retracting the tissues surrounding the surgical operating area by reducing the bulk of the instrumentation in order to ensure the best view of the operating area for the surgeon.

According to an advantageous alternative embodiment, the connection accessory is made up of a blade having a median area extended at either side by grooves allowing a relative longitudinal movement of the tubes inserted in said grooves.

BRIEF DESCRIPTION OF THE DRAWINGS

Further objectives and advantages of the invention will become apparent from the following description made in reference to the appended drawings, wherein.

DETAILED DESCRIPTION

Figure 1:
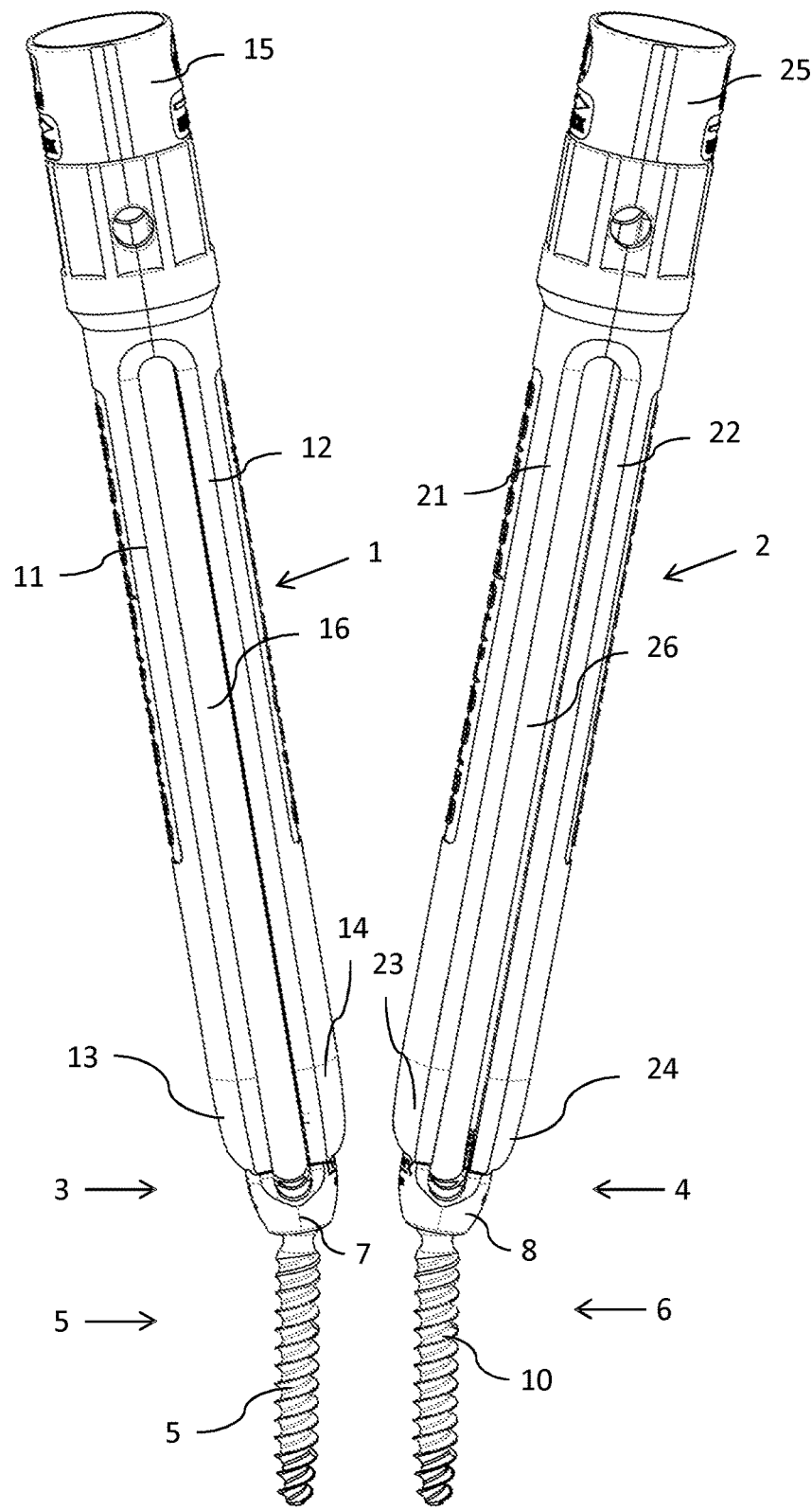
FIG. 1 is a perspective view of two tubes during the placement of screws in a vertebra

FIG. 1 is a profile view of two tubes (1, 2) during the placement of screws (5, 6) in a vertebra, with tubes known from the prior art. Each of said two tubes (1, 2) supports at the proximal end thereof (3, 4) a spinal (or "pedicular") screw (5, 6), which is advantageously pre-mounted. The connection between the proximal end (3, 4) and the screw (5, 6) is provided by means of a head (7, 8) having a fastening groove engaging with a shoulder provided on the inner surface of the proximal end (3, 4) of the tubes (1, 2).

The pedicular screws (5, 6) are intended for being fixed to vertebrae. Said screws include a bone-anchor means (9, 10) extended by a slotted head (7, 8) for receiving an intervertebral linking rod, not shown. When the rod is in place, a screwable plug (not shown) is screwed into the head (7, 8) via a thread, in order to lock the assembly.

The material most commonly used to manufacture the screws is titanium. In a specific configuration of the invention, the material used for manufacturing can be any implantable material, currently known or otherwise, such as PEEK, stainless steel, cobalt chromium, or even a fibreglass or carbon-fibre composite. Coatings such as HATCP (HydroxyApatite TriCalcium Phosphate) or others can also be applied to improve the bone anchoring or overall mechanical resistance of the implant.

The installation of said screw (5, 6) and the placement of the rod, followed by the locking thereof with the screwable plug are provided by an instrument described in prior art patent PCT/FR10/000880, the contents of which is included in the present application by reference to said PCT application.

The tubes (1, 2) are, in the described example, each made up of two half shells (11, 12), (21, 22), respectively, hingedly connected by the proximal ends thereof (13, 14), (23, 24) such as to allow tilting relative to the screw head (7, 8), when the two half shells are released.

A ring (15, 25) provides the locking of the two half shells (11, 12) such as to form tubes (1, 2) which are closed during certain phases of use.

The tubes (1, 2) have longitudinal openings (16, 26) allowing the insertion of a linking rod and the movement thereof into the U-shaped slot provided in the head (7, 8) of the screw.

It should be noted that the invention is not limited to the implementation of tubes formed by two half shells, and can also be applied to integral tubes.

However, the embodiment in the form of two assembled half shells is a preferred embodiment.

Detailed Description of the First Alternative Embodiment

Figure 2:
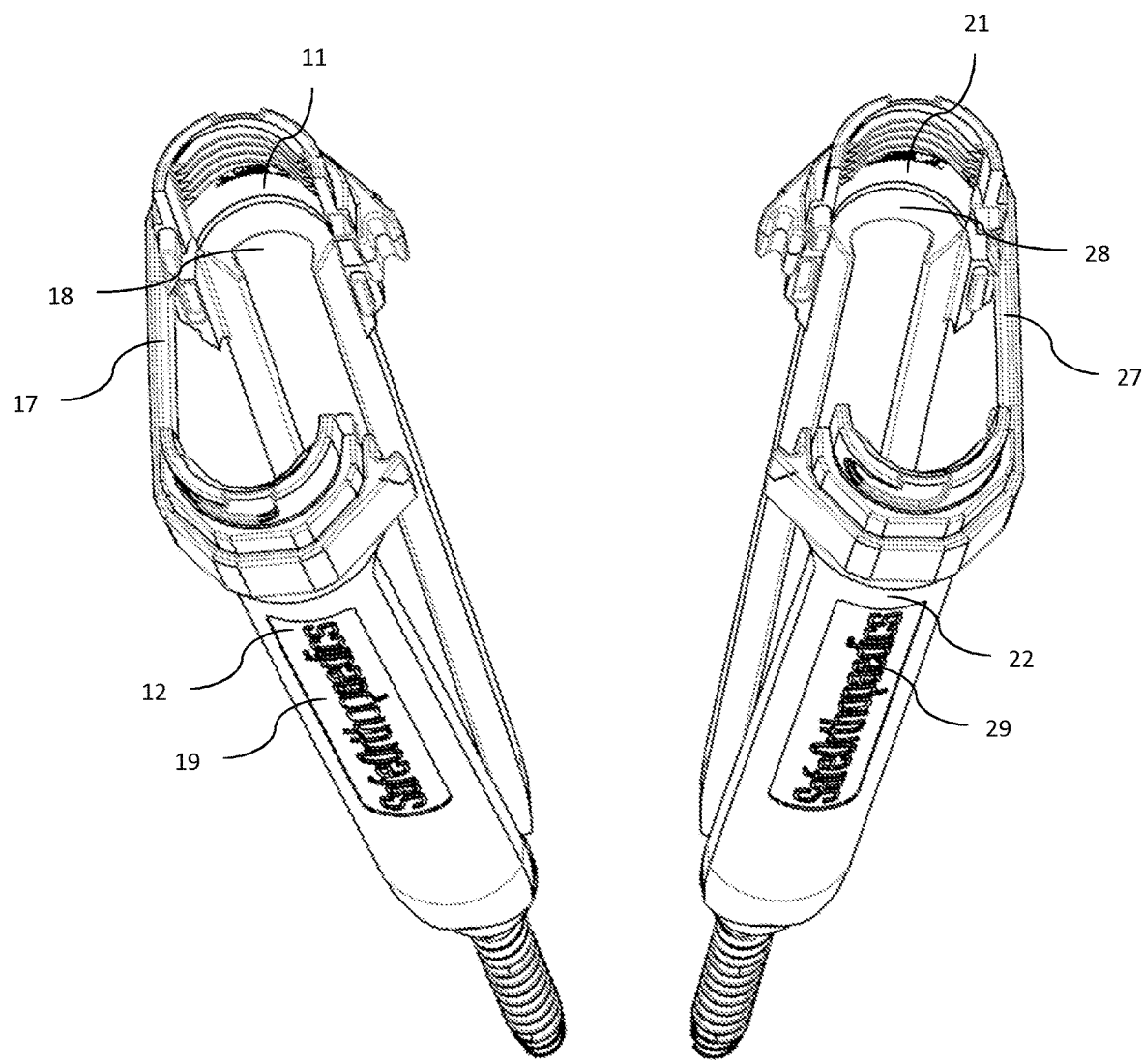
FIG. 2 is a perspective view of a first alternative embodiment of two tubes locked in open position by a first connection accessory

FIG. 2 is a perspective view of a first alternative embodiment of two tubes (1, 2) locked in open position by a first connection accessory (17, 27).

The tubes (1, 2) are not provided with the ring (15, 25) in order to allow the angular separation of the two half shells (11, 12), (21, 22).

Figure 3:
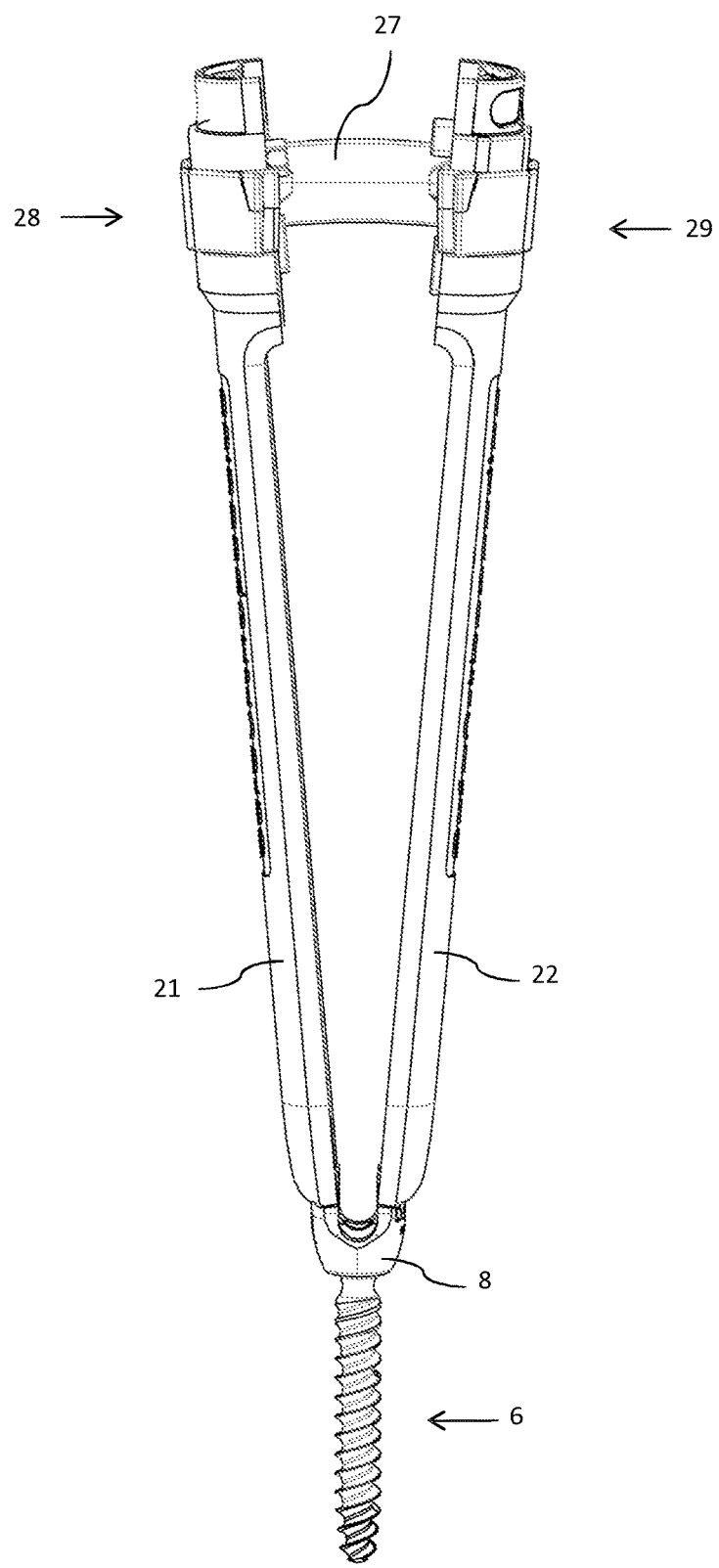
FIG. 3 is a profile view of the embodiment according to said first alternative embodiment, of a tube in locked open position

FIG. 2 shows a posterior dorsal implantation via tubes, an example of which is depicted in detail in FIG. 3. Each tube (1, 2) has a screw implanted in the pedicles of two separate vertebrae, which are not necessarily consecutive. The two tubes (1, 2) are offset according to a sagittal axis which is parallel to the spinal column. The half shells (11, 12), (21, 22) are open such as each to form an angle relative to the sagittal plane. Said opening makes it possible to free up the field of vision and work in the area where the corresponding screw will be installed.

The separation of the two half shells does not separate the tube (1, 2) from the head (7, 8) of the screw (5, 6) due to the hinged connection between said two parts via a shoulder engaging with a groove, as taught in aforementioned patent application PCT '880.

The half shells (11, 12), (21, 22) are kept in open position by a connection accessory (17, 27) which adapts to the distal ends (18, 19), (28, 29) of the half shells (11, 12), (21, 22).

Figure 4:
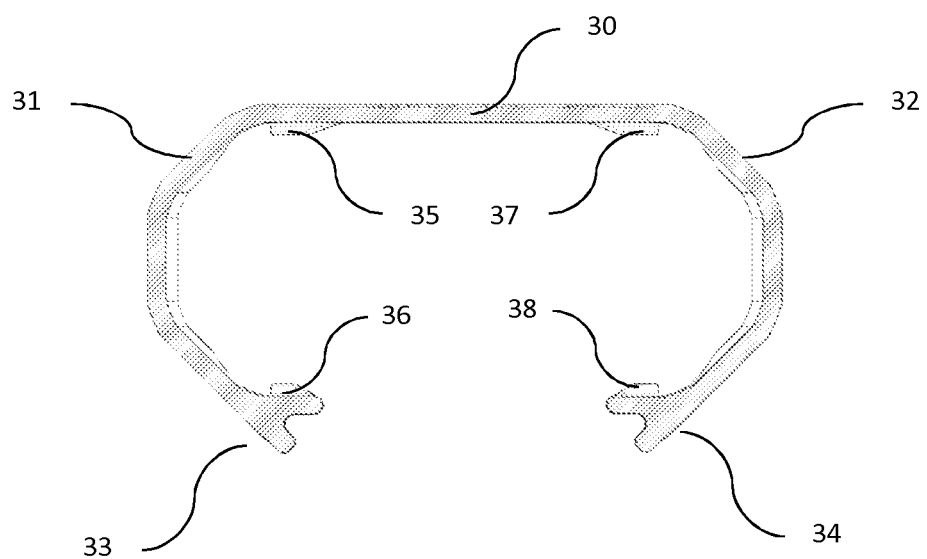
FIG. 4 is a section view of said first connection accessory

FIG. 4 is a detailed view of the connection accessory. Said accessory is made up of a generally C-shaped moulded plastic part in the described example. The median portion (30) has a length defining the angle of opening of the tube, when the accessory is placed on the two half shells.

By way of example, said median portion (30) has a length of 25 millimeters, for an angulation of 20 degrees between the two half shells (21, 22), when said portion has a length of 150 millimeters, measured between the area for connecting with the screw head and the area for connecting with the accessory.

The median portion (30) is extended at either side by an arched portion (31, 32), the inner section of which can match the outer surface of the outer surface of the distal ends (18, 19), (28, 29) of the half shells (11, 12), (21, 22).

The opening of said arched portions (31, 32) is determined such as to enable engagement by resilient deformation on said distal ends (18, 19), (28, 29) of the half shells (11, 12), (21, 22), and to ensure holding by snap-fitting.

Each arched portion (31, 32) is extended by a tab (33, 34) allowing easy the removal thereof. Said tabs (33, 34) make it possible to exert radial forces in order to open the arched portion, when seeking to remove the accessory.

The inner surface of the accessory also has lugs (35 to 38) which are inserted in matching cavities provided on the inner surface of said distal ends (18, 19), (28, 29) of the half shells (11, 12), (21, 22), and improve positioning and holding of the accessory.

The two half tubes act as a lateral retractor when locked in open position by the accessory according to the first alternative embodiment, without it being necessary to insert any additional tools in the incision.

Detailed Description of the Second Alternative Embodiment

Figure 5:
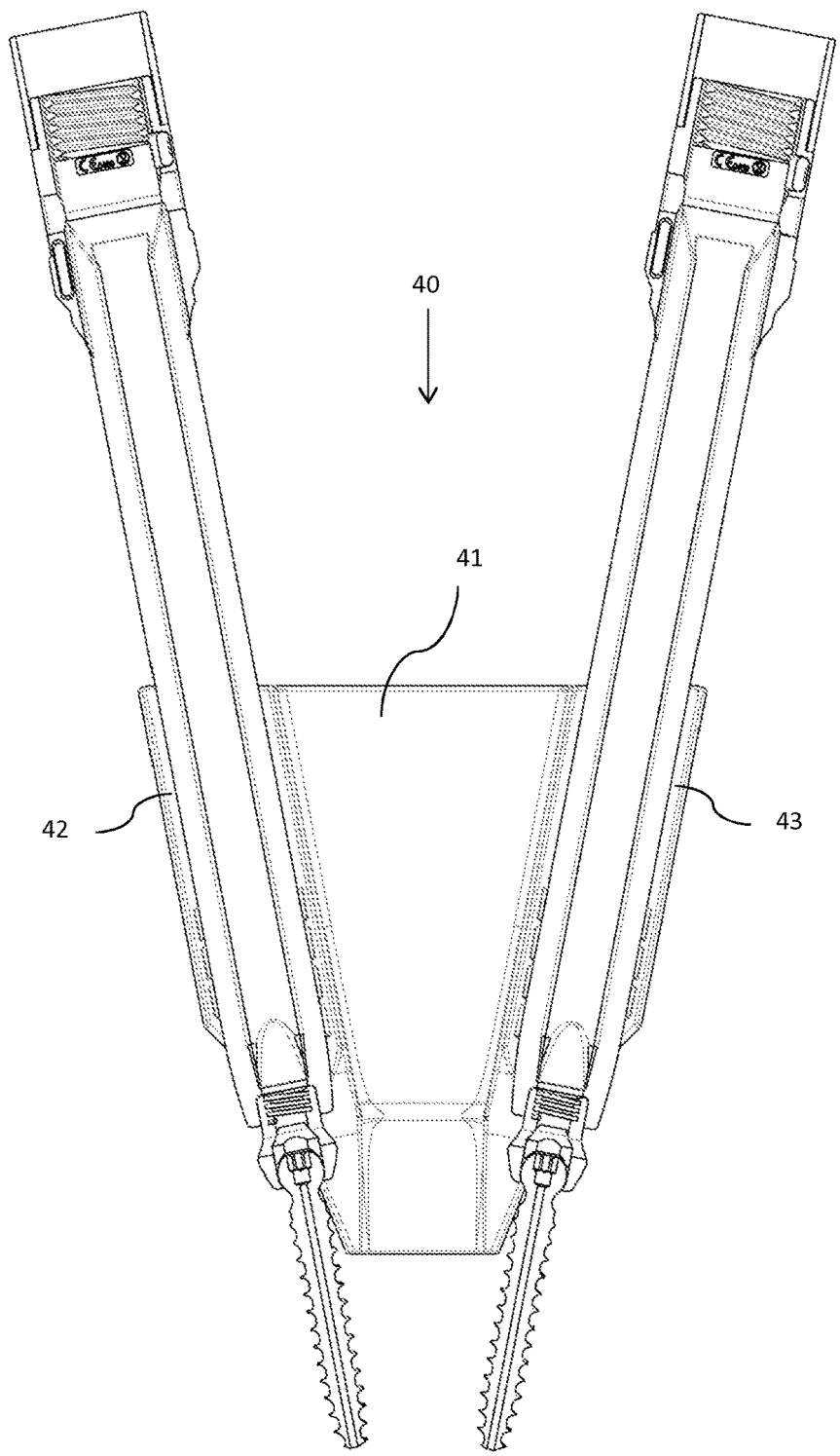
FIG. 5 is a sagittal cutaway view of a second alternative embodiment of the two tubes connected by a second connection accessory

FIG. 5 is a sagittal cutaway view of a second alternative embodiment of the half shells of two tubes connected by a second connection accessory.

Said accessory cannot be used to connect the two half shells of a single tube in order to exercise lateral pressure, in a direction perpendicular to the sagittal plane, as provided for the first alternative embodiment.

The accessory can be used to connect two separate tubes, which can be integral or made up of two half shells, and to position an accessory forming a retractor, extending in a longitudinal direction.

Said accessory is made up of a plastic part (40) in the described example. It has a median area (41) in the form of a thin frusto-conical segment, such as to form a convex web, extended at either side by a groove (42, 43) with a shape that matches the outer section of said tubes.

Figure 6:
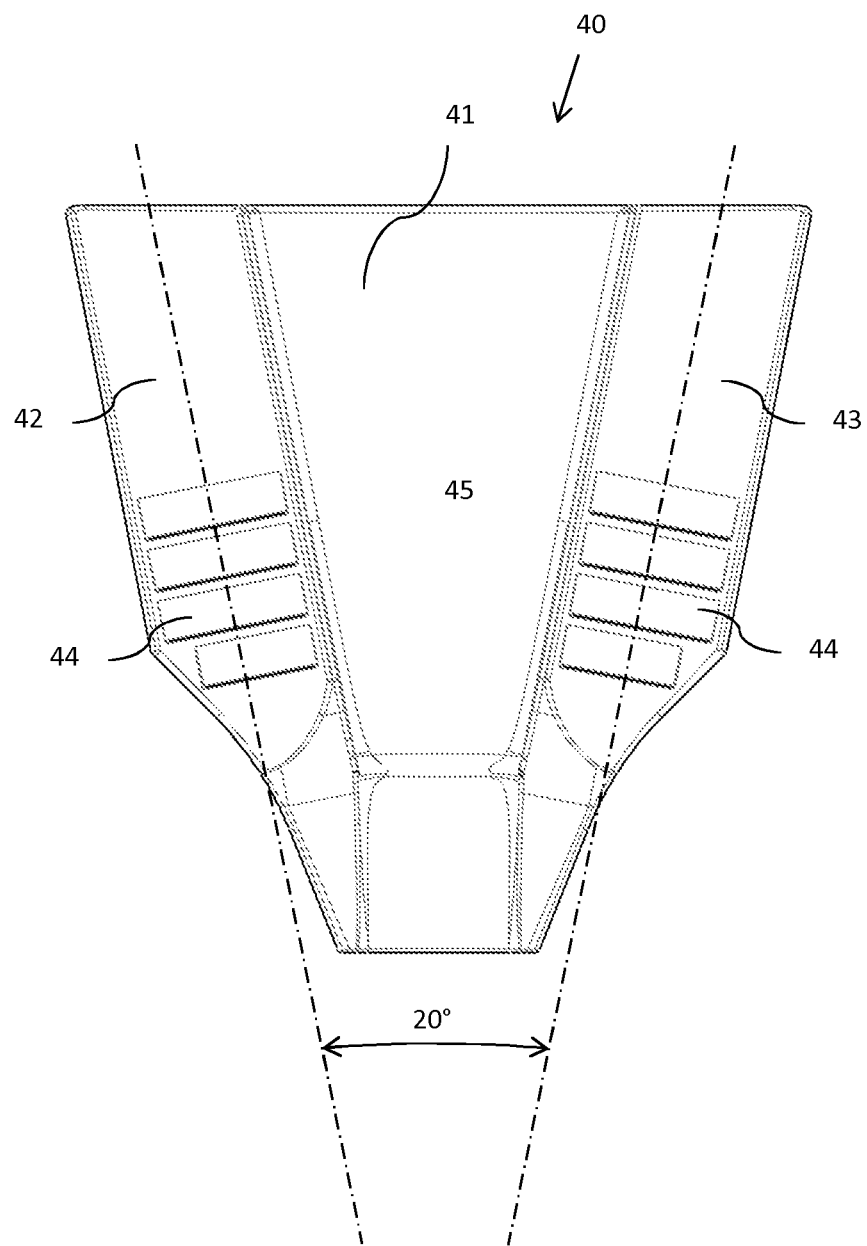
FIG. 6 is a view according to a first embodiment of said second connection accessory, in a profile view

The two grooves (42, 43) have axes that converge in the proximal direction, with an angle of around 20 degrees. The inner surface of said grooves (42, 43) can have flutes (44) as shown in FIG. 6, to ensure vertical holding relative to the tubes (1, 2). Other fastening modes are foreseeable, for example one or more studs, lugs or projections which engage with one more matching recesses provided on the outer surface of the tubes (1, 2). Said studs, lugs or projections are preferably configured to allow longitudinal movement of the tubes relative to the grooves, for example with indexed positions.

The longitudinal movement of the accessory relative to the tubes causes a variation in the separation of the proximal ends of the tubes (1, 2) and consequently exerts a stress to separate the screws anchored to the vertebrae and to the tubes (1, 2). This makes it possible to improve the view of the intervertebral operating area, facilitating the surgical deed, for example and then the insertion of an intersomatic cage by transforaminal approach. Pushing the accessory in the proximal direction thus causes a forced opening of the intervertebral space.

FIG. 6 also shows that the central area (41) has a first distal portion (45) in the form of a frusto-conical tile with a section that decreases towards the proximal direction, extended by a second proximal portion (46) in the form of a cylindrical tile, flared relative to the first distal portion (45). The axis of symmetry of said second portion forms a divergent angle with the axis of symmetry of the first portion, such that the distal area of the accessory pushes the tissues near the vertebrae outwards when it is inserted in the surgical operating area.

Figure 7:
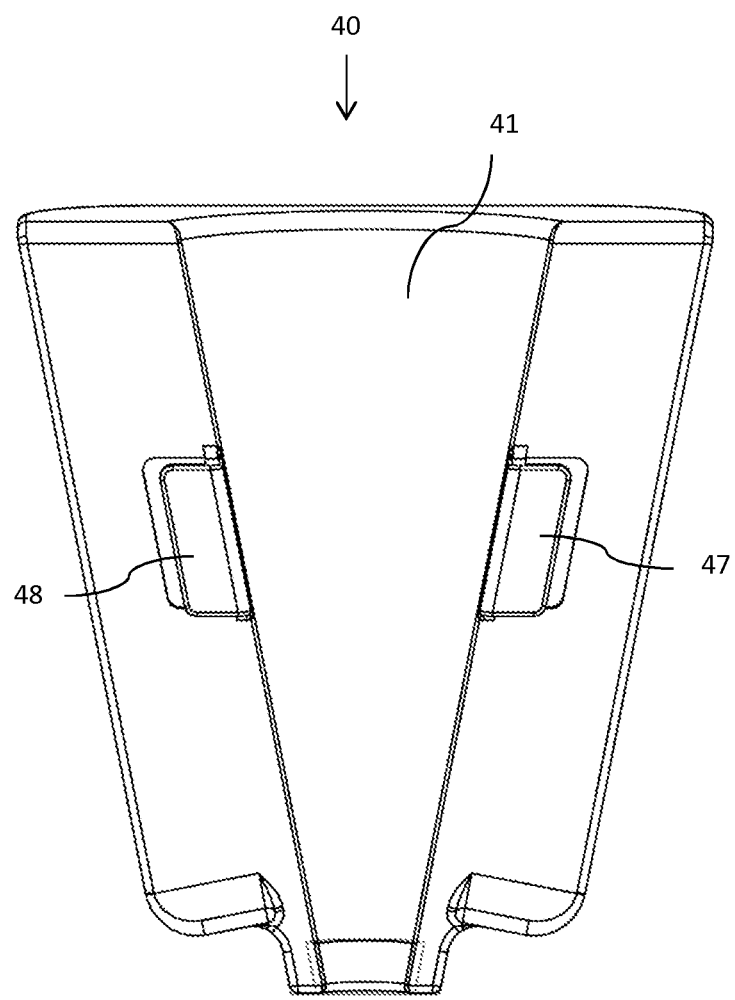
FIG. 7 is a view according to a second embodiment of said second connection accessory, in a profile view

The grooves can be replaced with lugs (47, 48) providing the same function of anchoring the accessory to the tubes (1, 2) as shown in FIG. 7.

Figure 8:
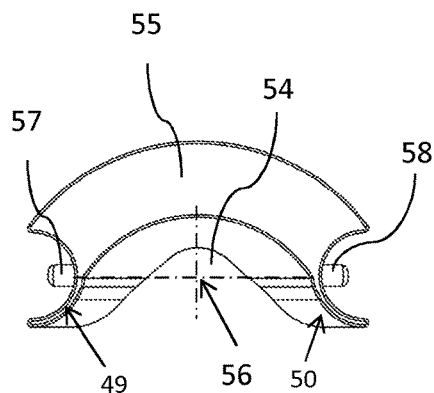
FIGS. 8 to 10 are top, profile and side views, respectively, according to a third embodiment of said second connection accessory.
Figure 9:
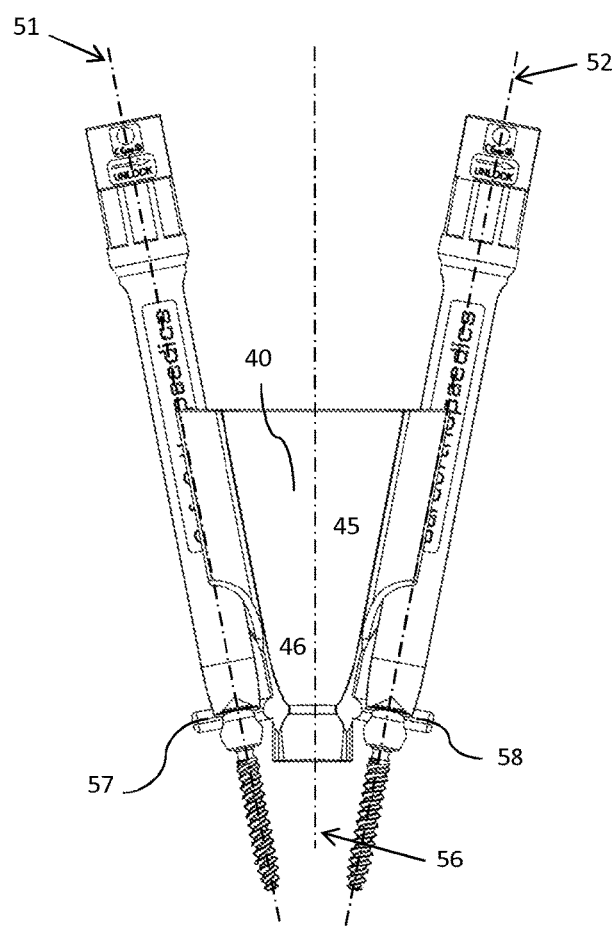
Figure 10:
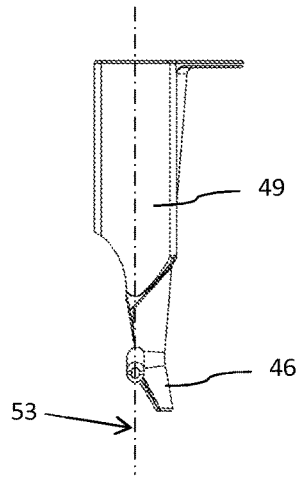

FIGS. 8 to 10 show an alternative embodiment in which the grooves (42, 43) rest on the outer surfaces (49, 50) of the tubes (1, 2), on either side of the longitudinal channel (16, 26) of the related tube (1, 2). The median area (40) forms a frusto-conical web extending from one groove (42) to the other (43), such as to create an opening of around 20° between the longitudinal axes of the two grooves (42, 43). Said web has a regular curve, with no sharp corners that might damage the separated tissues. When the accessory is in place, it opens up an empty frusto-conical inner space (54) constituting a working area allowing the insertion of surgical instruments such as disc clamps or Kerrison clamps (commercial name) or an intersomatic cage. The opening section of said frusto-conical working area has a radius of around 40 millimeters, and is restricted such as to reach a radius of around 15 millimeters at the distal end. The length of said working area is comprised between c and 100 millimeters.

A flange (55) extends in a plane substantially perpendicular to the median axis (56) of the accessory, over a width of around 10 millimeters. Said flange (55) provides the reinforcement of the part and makes same easier to handle.

At the proximal end, opposite said flange (55), the web (41) has a flared cylindrical enlargement (46).

Each one of the grooves (42, 43) has on the bearing surface thereof on the tube (1, 2) a lug (57, 58) with a length of around 10 millimeters and a section corresponding to the opening of the channel (16, 26) of the tubes (1, 2) and to the U-shaped recess provided in the head of the spinal screws (7, 8). Said lugs are inserted in the screw heads when the accessory is pushed back in the proximal direction. They thus lock and immobilise the assembly by means of the insert or a plug inserted in the tube (1, 2).

Figure 11:
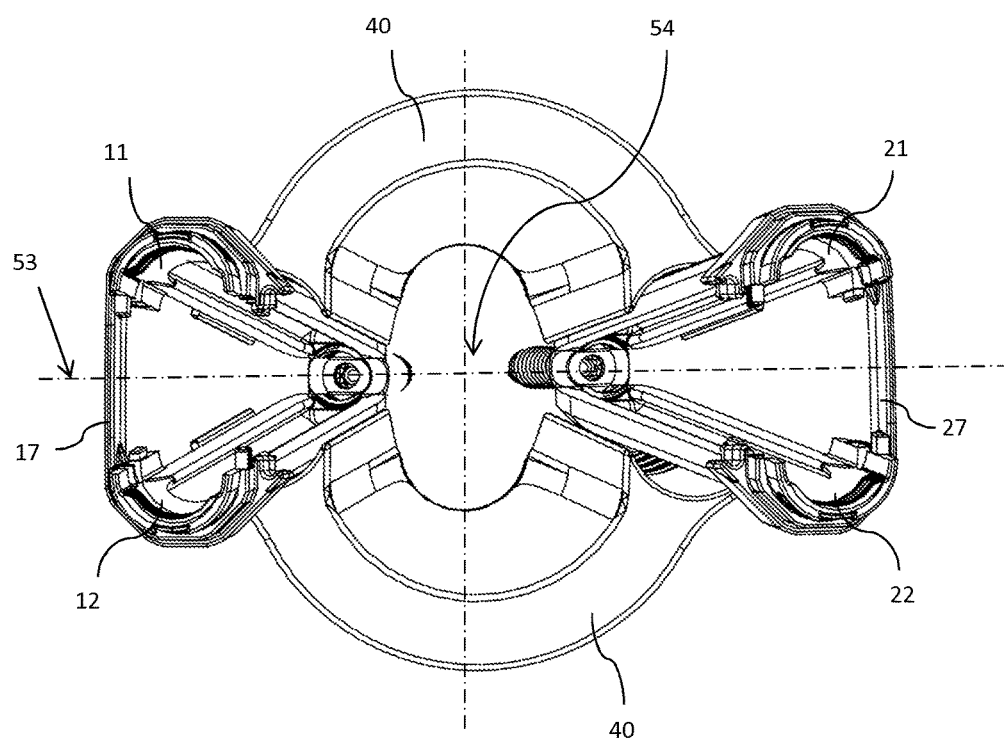
FIG. 11 is a top view of an embodiment combining said first and second connection accessories.

FIG. 11 shows an example of an embodiment of a system using the two types of accessories.

The tubes (1, 2) are separated relative to a longitudinal plane (53) in open position, the half shells (11, 12; 21, 22) being locked by first accessories (17, 27).

They are also separated relative to a sagittal plane (59), perpendicular to the longitudinal plane (53), by means of second accessories (40).

The assembly defines a frusto-conical working area (54).

Figure 12:
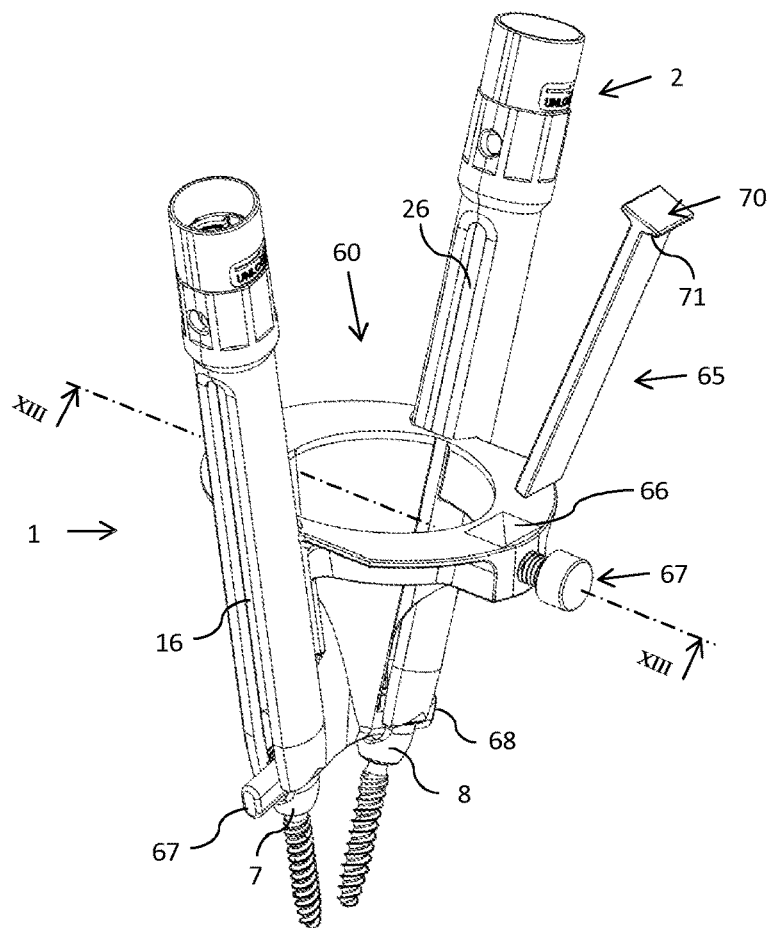
FIG. 12 is a perspective view of a third alternative embodiment of the two tubes connected by a third connection accessory.
Figure 13:
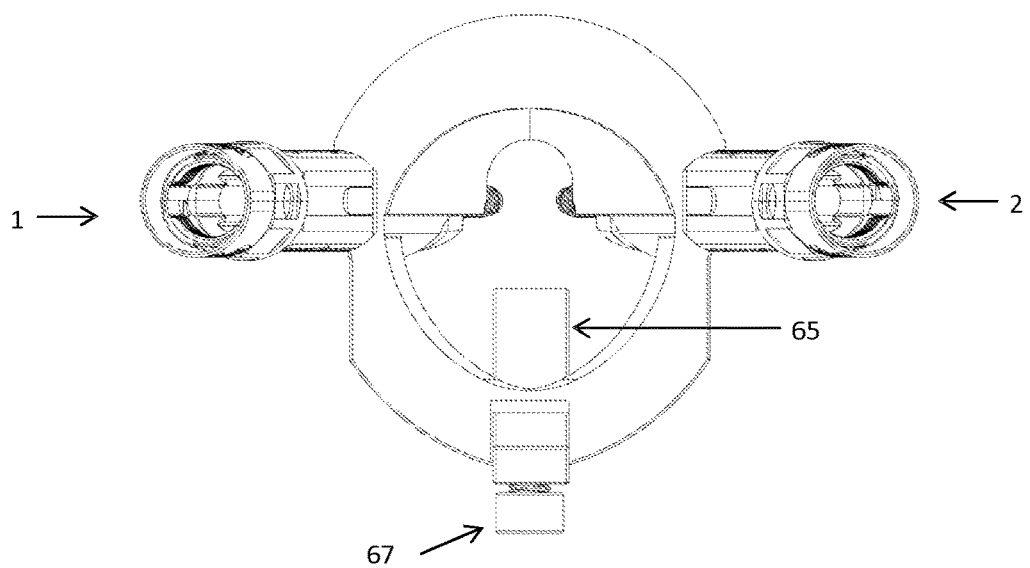
FIG. 13 is a top view of the embodiment of the third alternative embodiment shown in FIG. 12.

FIG. 12 is a perspective view of a third alternative embodiment of two tubes connected by a third connection accessory.

Figure 15:
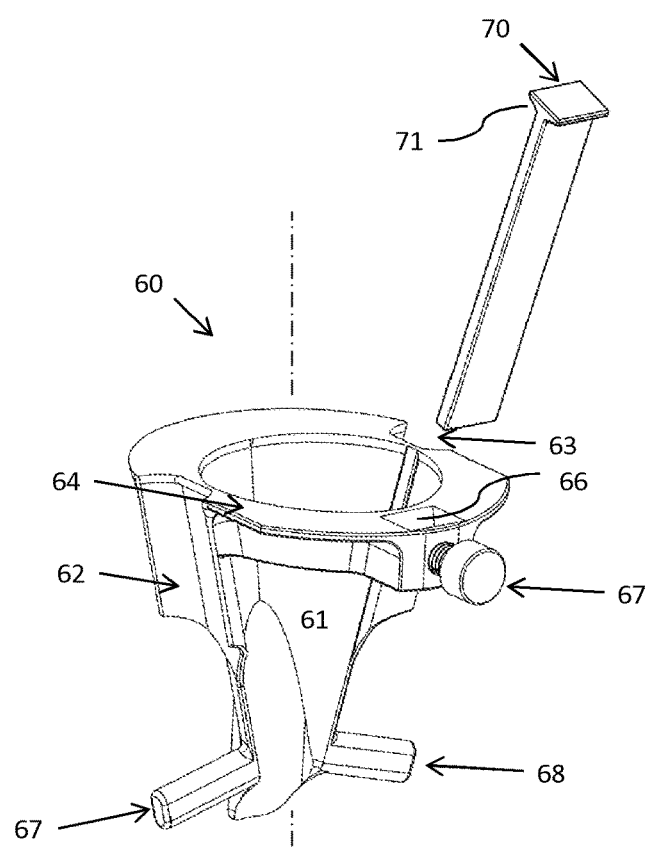
FIG. 15 is a schematic view of the accessory.

The third connection accessory (60), shown in FIG. 15, has the essential characteristics of the connection accessory shown in FIG. 9. In particular, said accessory comprises a median area (61) in the form of a thin frusto-conical segment such as to form a convex web. The median area (61) is extended at either side by a groove (62, 63) with a shape that matches the outer section of the tubes (1, 2). More specifically, the grooves (62, 63) are arranged diametrically opposite one another. They are furthermore arranged such as to rest on the outer surface of the tubes (1, 2), on either side of the longitudinal channel (16, 26) of the related tube (1, 2), as shown in FIG. 12. Likewise, the third connection accessory (60) comprises, at the proximal end, two lugs (67, 68) extending on either side of the median area (61). Each lug (67, 68) has a section corresponding to the opening of the channel (16, 26) of the tubes (1, 2) and to the U-shaped recess provided in the head of the spinal screws (7, 8). As previously indicated, such lugs make it possible to lock and immobilise the tube and spinal screw assembly when the connection accessory (60) is positioned on the tubes (1, 2), the lugs (7, 8) being arranged in the U-shape of the screw heads (7, 8).

In said alternative embodiment, however, the median area (61) is extended, at the distal end thereof, by a semi-circular crown (64) extending from one groove (62) to the other groove (63). The semi-circular crown (64) extends in a plane substantially perpendicular to the median axis (56) of the accessory. It defines, with the distal end of the median area (61), an entrance opening to a working area for passing surgical instruments or implants. In the depicted embodiment, the semi-circular crown (64) is formed integrally with the median area (61).

The semi-circular crown (64) comprises a through-hole (66) for passing a removable blade (65) from the distal end of the accessory to the proximal end. Advantageously, the through-hole (66) is placed equidistant from the two grooves (62, 63). When mounted on the crown, the removable blade (65) defines, together with the frusto-conical web, the working area. As will be understood below, the removable blade (65) is a hingedly connected blade.

In the depicted embodiment, the removable blade (65) is blocked on the semi-circular crown (64) by means of a locking screw (67) mounted in a through-hole made in the outer surface of the semi-cylindrical crown and opening out at the through-hole (66) of the removable blade (65). It is obvious that other means can be provided for blocking the blade without departing from the context of the invention.

Figure 14:
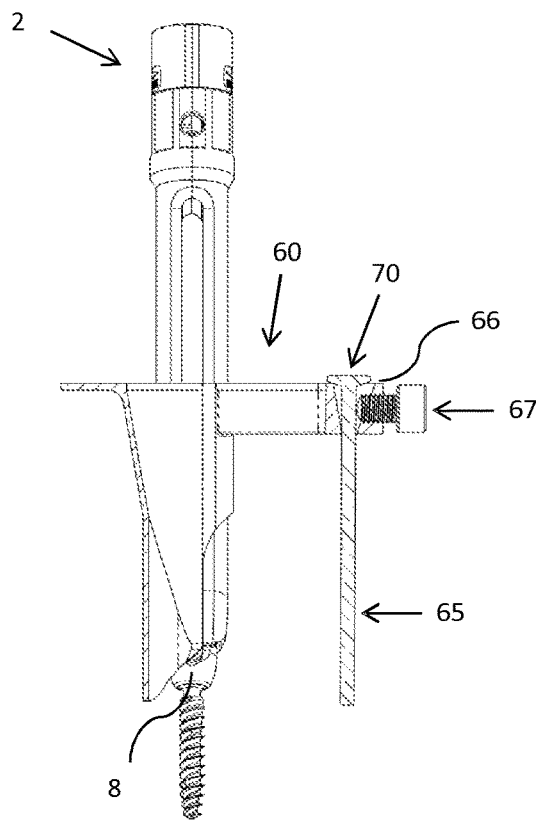
FIG. 14 is a perspective view of the third connection accessory.

As shown in FIG. 14, the through-hole (66) has a funnel shape which narrows in a direction opposite the distal end of the accessory (60). It also has, at the outlet, a section which is slightly larger than the section of the removable blade (65). Said configuration thus makes it possible not only to facilitate the insertion of the blade (65) in the hole (66) but also to widen the working area by tilting said blade in the through-hole (66) from a position in which the removable blade converges towards the proximal end of the frusto-conical web towards a substantially vertical position (FIG. 14).

Advantageously, the removable blade (65) comprises a gripping means (70) at the distal end. In the example shown, the gripping means is depicted by a T shape (71).

The invention claimed is:

1. A spinal device for carrying out a surgical procedure on vertebrae by a posterior or posterolateral approach, comprising:
    at least one tube and at least one spinal screw capable of engaging with the proximal end of said tube,
    a connection accessory, comprising a median portion extended at either side by reversible fastening means to at least one of said tubes, said connection accessory being configured such as to keep at least one of said tubes in an open angular position;
    wherein said reversible fastening means comprises an arched portion forming a groove having an inner section matching an outer surface of said at least one of said tubes.

2. A spinal device according to claim 1, wherein said connection accessory is made up of a rigid retraction blade capable of engaging with two separate tubes and of keeping the tissues in the area around the surgical field separated by locking the relative position of two tubes.

3. The connection accessory according to claim 2, wherein said blade is made up of a median area extended at either side by a groove allowing a relative longitudinal movement of the tubes inserted in said grooves.

4. The connection accessory according to claim 2, wherein a median area has a first distal portion in the form of a frusto-conical tile with a section that decreases in the proximal direction, extended by a second proximal portion in the form of a cylindrical tile, flared relative to the first distal portion.

* * * * *